(12) United States Patent
Jun

(10) Patent No.: US 9,470,653 B2
(45) Date of Patent: Oct. 18, 2016

(54) METHOD AND APPARATUS FOR DIAGNOSING DISCONNECTION OF OXYGEN SENSOR

(71) Applicant: Hyundai Autron Co., Ltd., Seongnam-si (KR)

(72) Inventor: Young Ho Jun, Suwon-si (KR)

(73) Assignee: HYUNDAI AUTRON CO., LTD., Seongnam-Si (KR)

( * ) Notice: Subject to any disclaimer, the term of this patent is extended or adjusted under 35 U.S.C. 154(b) by 0 days.

(21) Appl. No.: 14/806,636

(22) Filed: Jul. 22, 2015

(65) Prior Publication Data

US 2016/0091459 A1    Mar. 31, 2016

(30) Foreign Application Priority Data

Sep. 30, 2014    (KR) .................. 10-2014-0130752

(51) Int. Cl.
*G01N 27/409* (2006.01)
*G01N 27/416* (2006.01)
*G01N 27/406* (2006.01)

(52) U.S. Cl.
CPC ...... *G01N 27/4163* (2013.01); *G01N 27/4065* (2013.01); *F01N 2560/025* (2013.01); *G01N 27/409* (2013.01)

(58) Field of Classification Search
CPC ........... G01N 27/4065; G01N 27/407; G01N 27/409; F01N 2560/025; F01N 2560/026
See application file for complete search history.

(56) References Cited

U.S. PATENT DOCUMENTS 4,951,632 A * 8/1990 Yakuwa ............. G01N 27/4175
123/688

FOREIGN PATENT DOCUMENTS

KR    10-2010-0094206 A    8/2010
KR    10-2012-0124691 A    11/2012

OTHER PUBLICATIONS

Machine-generated English language translation of Korean Intellectual Property Office (KIPO), Office Action of Korean Patent Application No. 10-2014-0130752, Jul. 21, 2015. Obtained from KIPO website.*
Machine-generated English language translation of Korean Intellectual Property Office (KIPO), Written Opinion for Korean Patent Application No. 10-2014-0130752, Sep. 21, 2015. Obtained from KIPO website.*
KIPO machine-generated English langauge translation of KR 10-2009-0013521, patent published Aug. 26, 2010.*
Korean Intellectual Property Office, Office Action for Korean Patent Application No. 10-2014-0130752, Jul. 21, 2015, entirely in Korean.

* cited by examiner

*Primary Examiner* — Alexander Noguerola
(74) *Attorney, Agent, or Firm* — Mayer Brown LLP; Hyunho Park

(57) ABSTRACT

A method for diagnosing disconnection of an oxygen sensor includes measuring, by a controller, a voltage supplied to an oxygen sensor through a voltage divider; measuring a voltage of a reference cell of the oxygen sensor; determining whether the voltage supplied to the oxygen sensor and the voltage of the reference cell fall within a reference range from preset reference values, respectively; and determining that a ground wire of the oxygen sensor is disconnected, when the voltage of the oxygen sensor or the voltage of the reference cell deviates from the reference range.

10 Claims, 3 Drawing Sheets

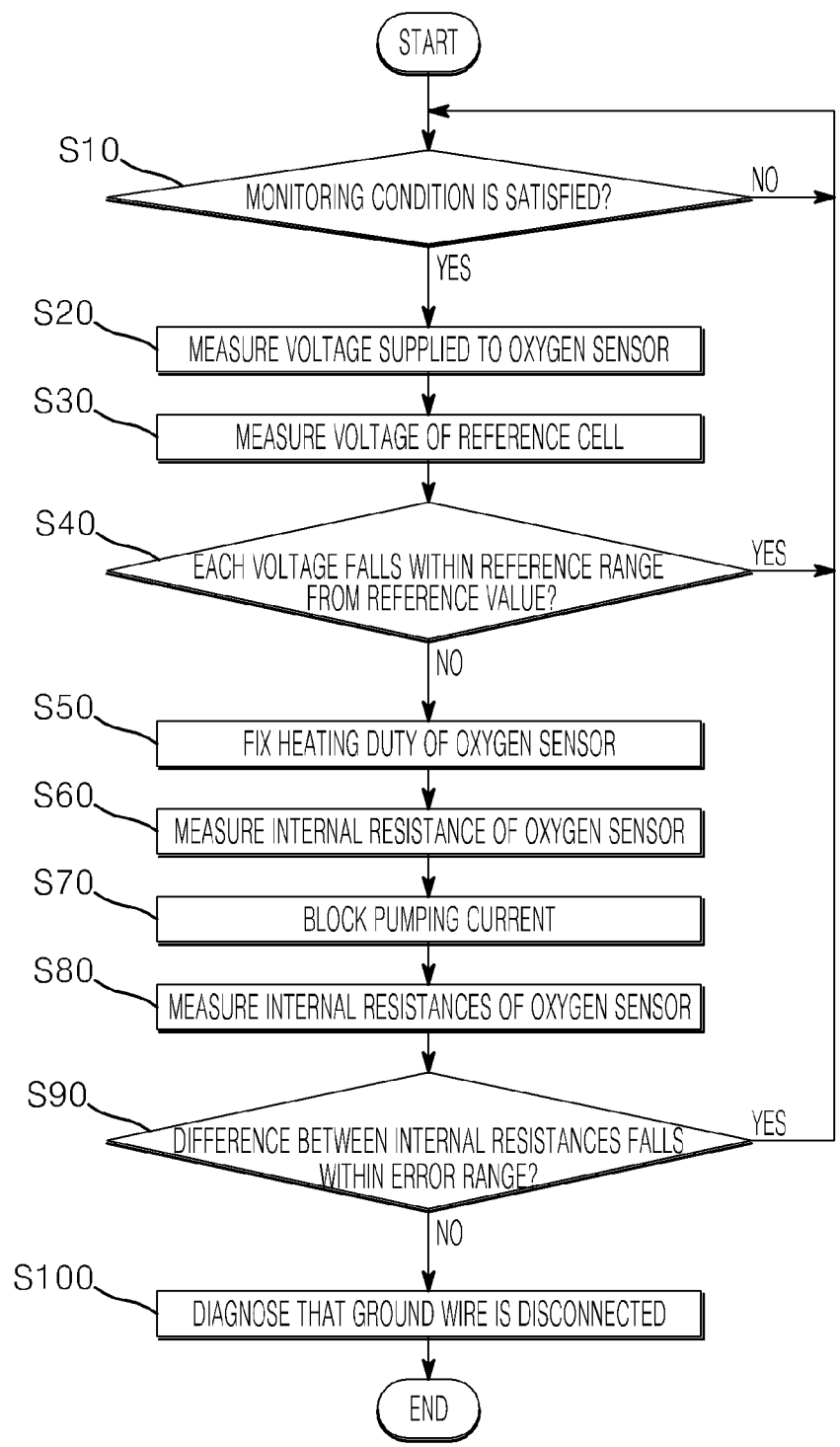

METHOD AND APPARATUS FOR DIAGNOSING DISCONNECTION OF OXYGEN SENSOR

CROSS-REFERENCE TO RELATED APPLICATIONS

The present application claims priority to Korean application number 10-2014-0130752, filed on Sep. 30, 2014, which is incorporated by reference in its entirety.

BACKGROUND OF THE INVENTION

The present invention relates to a method and apparatus for detecting disconnection of an oxygen sensor, and more particularly, a method and apparatus for diagnosing disconnection of an oxygen sensor, which is capable of measuring a voltage and internal resistance of the oxygen sensor and determining whether a ground wire of the oxygen sensor is disconnected, based on the measured values.

Recently, due to the acceleration of environmental pollution, restrictions on exhaust gas having a large influence on air pollution have been strengthened in the automobile industry.

Each country forces automobile manufacturers to reduce exhaust gas through various regulations.

So far, a method has been developed and widely used to reduce exhaust gas of a vehicle. According to the method, a catalytic converter is attached to an exhaust pipe so as to filter harmful gas contained in exhaust gas, or the concentration of oxygen contained in exhaust gas is measured through an oxygen sensor in order to burn fuel at an optimal air-fuel ratio.

That is, based on the oxygen concentration of the exhaust gas, sensed through the oxygen sensor, the amount of air required for burning fuel is fed back to adjust a fuel injection amount at the optimal air-fuel ratio at which the smallest amount of harmful gas is discharged.

The related art of the present invention is disclosed in Korean Patent Laid-open Publication No. 2012-0124691 published on Nov. 14, 2012 and entitled "Method for diagnosing oxygen sensor of vehicle".

When the oxygen sensor breaks down, the oxygen sensor cannot precisely measure the oxygen concentration of exhaust gas. Thus, much attention is being paid to a technology for diagnosing a failure of an oxygen sensor.

That is, when a disconnection or short fail occurs in the oxygen sensor such that the oxygen sensor does not perform a normal operation, the air-fuel ratio cannot be controlled because the oxygen sensor cannot determine whether the current air-fuel ratio is higher or lower than a theoretical air-fuel ratio.

Furthermore, since the amount of harmful gas contained in the exhaust gas may increase in a state where the air-fuel ratio cannot be controlled, there is an increasing need for a technology capable of precisely determining whether an oxygen sensor is normally operated.

According to the recent trend, monitoring parts related to exhaust gas of a vehicle and diagnosing a failure through OBD (On Board Diagnosis) have been mandatory.

BRIEF SUMMARY

Embodiments of the present invention are directed to a method and apparatus for diagnosing disconnection of an oxygen sensor, which is capable of measuring a voltage and internal resistance of an oxygen sensor, and determining whether a ground wire of the oxygen sensor is disconnected, based on the measured values.

In one embodiment, a method for diagnosing disconnection of an oxygen sensor may include: measuring, by a controller, a voltage supplied to an oxygen sensor through a voltage divider; measuring a voltage of a reference cell of the oxygen sensor; determining whether the voltage supplied to the oxygen sensor and the voltage of the reference cell fall within reference ranges from preset reference values, respectively; and determining that a ground wire of the oxygen sensor is disconnected, when the voltage supplied to the oxygen sensor or the voltage of the reference cell deviates from its reference range.

The method may further include determining whether the oxygen sensor is activated and an engine is normally driven, before measuring the voltage supplied to the oxygen sensor. When the oxygen sensor is activated and the engine is normally driven, the controller may measure the voltage supplied to the oxygen sensor.

In the determining of whether the oxygen sensor is activated and the engine is normally driven, the controller may determine that the oxygen sensor is activated when the temperature of the oxygen sensor is equal to or more than a first reference temperature and the temperature of an exhaust pipe is equal to or more than a second reference temperature, and determine that the engine is normally driven when a battery voltage is equal to or more than a preset reference voltage, an engine RPM is equal to or more than a preset reference speed, and fuel injection of an injector is normally performed.

The method may further include comparing internal resistances of the oxygen sensor before and after a pumping current supplied to the reference cell through a pump cell of the oxygen sensor is blocked, before determining that the ground wire of the oxygen sensor is disconnected. When a difference between the internal resistances before and after the pumping current is blocked deviates from a preset error range, the controller may determine that the ground wire of the oxygen sensor is disconnected.

The comparing of the internal resistances of the oxygen sensor before and after the pumping current is blocked may include: fixing, by the controller, a heating duty of the oxygen sensor; measuring the internal resistance of the oxygen sensor before the pumping current is blocked; measuring the internal resistance of the oxygen sensor after the pumping current is blocked; and comparing the measured internal resistances of the oxygen sensor.

In another embodiment, an apparatus for diagnosing disconnection of an oxygen sensor may include: an oxygen sensor including a reference cell, a pump cell, and a measurement cell; a voltage divider configured to supply a voltage to the oxygen sensor through voltage division; and a controller configured to diagnose disconnection of the oxygen sensor through a pulse signal. The controller may measure the voltage supplied to the oxygen sensor through the voltage divider, sense a voltage of the reference cell of the oxygen sensor, and determine that a ground wire of the oxygen sensor is disconnected when the voltage supplied to the oxygen sensor and the voltage of the reference cell deviate from reference ranges from preset reference values, respectively.

The controller may measure the voltage supplied to the oxygen sensor when the oxygen sensor is activated and an engine is normally driven, and include an input unit configured to receive various signals for determining whether the oxygen sensor is activated and the engine is normally driven.

The controller may determine that the oxygen sensor is activated when the temperature of the oxygen sensor is equal to or more than a first reference temperature and the temperature of an exhaust pipe is equal to or more than a second reference temperature, and determine that the engine is normally driven when a battery voltage is equal to or more than a preset reference voltage, an engine RPM is equal to or more than a preset reference speed, and fuel injection of an injector is normally performed.

The controller may compare internal resistances of the oxygen sensor before and after a pumping current supplied to the reference cell through the pump cell of the oxygen sensor is blocked, and determine that the ground wire of the oxygen sensor is disconnected when a difference between the internal resistances before and after the pumping current is blocked deviates from a preset error range.

The controller may fix a heating duty of the oxygen sensor, and measure the internal resistance of the oxygen sensor before the pumping current is blocked.

BRIEF DESCRIPTION OF THE DRAWINGS

FIG. 3 is a flowchart for describing a method for diagnosing disconnection of an oxygen sensor in accordance with an embodiment of the present invention.

DETAILED DESCRIPTION

Embodiments of the invention will hereinafter be described in detail with reference to the accompanying drawings. It should be noted that the drawings are not to precise scale and may be exaggerated in thickness of lines or sizes of components for descriptive convenience and clarity only. Furthermore, the terms as used herein are defined by taking functions of the invention into account and can be changed according to the custom or intention of users or operators. Therefore, definition of the terms should be made according to the overall disclosures set forth herein.

Figure 1:
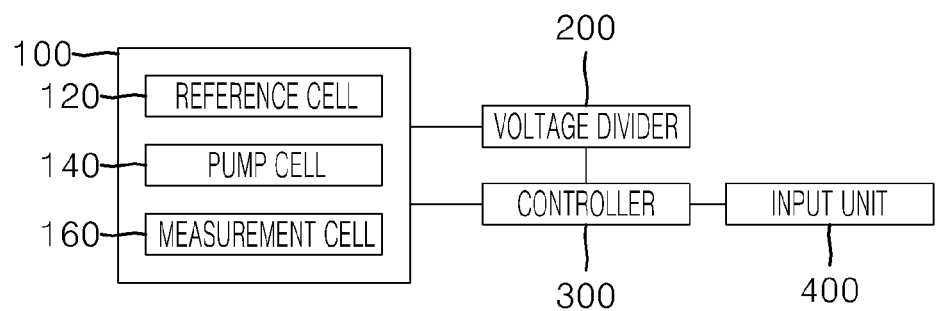
FIG. 1 is a functional block diagram of an apparatus for diagnosing disconnection of an oxygen sensor in accordance with an embodiment of the present invention.

FIG. 1 is a functional block diagram of an apparatus for diagnosing disconnection of an oxygen sensor in accordance with an embodiment of the present invention.

Figure 2:
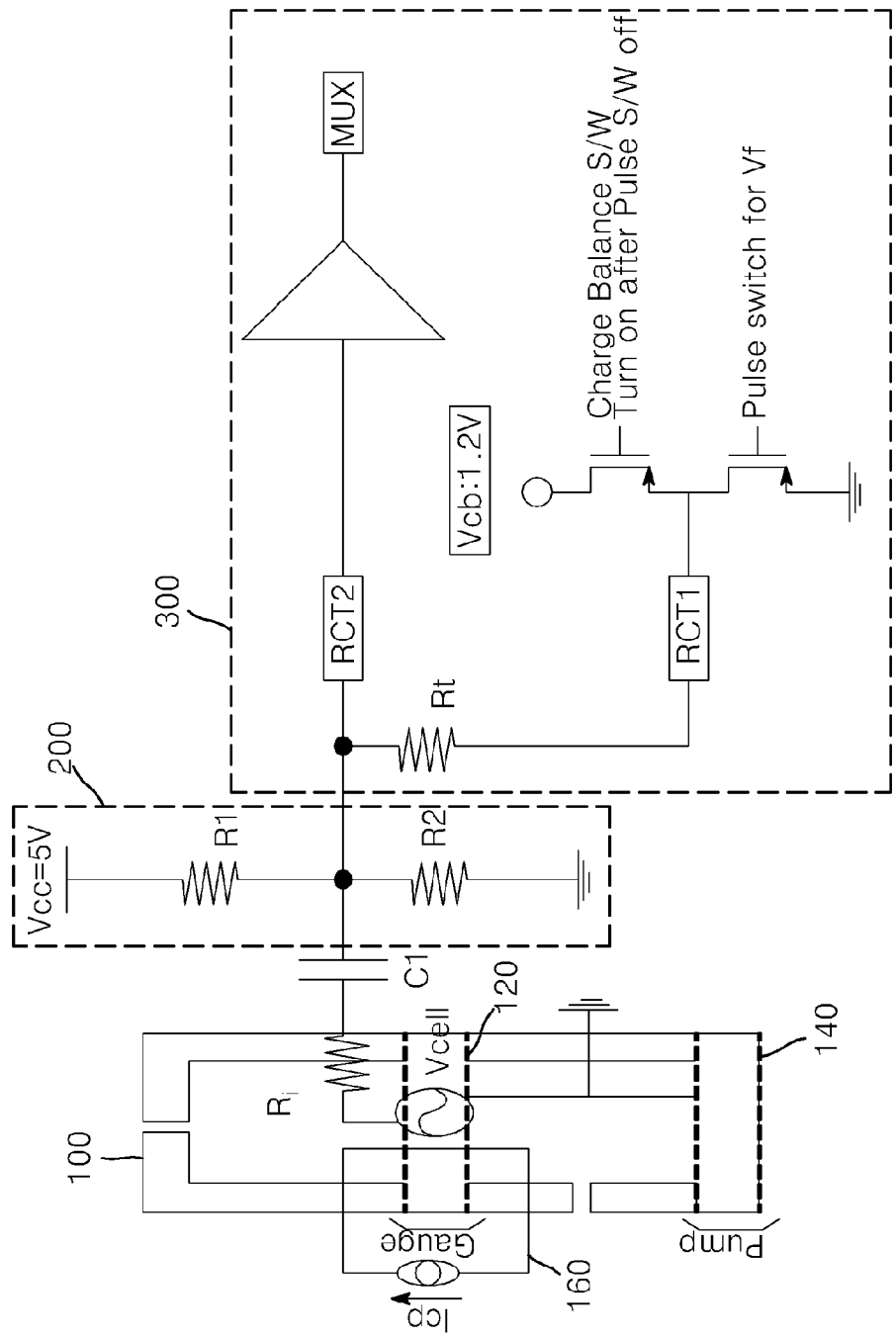
FIG. 2 is a circuit diagram illustrating a configuration for applying a pulse signal to an oxygen sensor in accordance with the embodiment of the present invention.

FIG. 2 is a circuit diagram illustrating a configuration for applying a pulse signal to an oxygen sensor in accordance with the embodiment of the present invention.

Referring to FIGS. 1 and 2, the apparatus for diagnosing disconnection of an oxygen sensor may include an oxygen sensor 100, a voltage divider 200, and a controller 300.

The oxygen sensor 100 may serve to sense the concentration of oxygen contained in exhaust gas of a vehicle, and include a reference cell 120, a pump cell 140, and a measurement cell 160. The reference cell 120 may include a space to which oxygen can migrate based on the oxygen concentrations of exhaust gas and atmospheric gas, the pump cell 140 may supply a pumping current required for a normal operation of the reference cell 120, and the measurement cell 160 may measure the concentration of oxygen contained in the exhaust gas based on the operation of the reference cell 120.

That is, the oxygen sensor 100 may generate an electromotive force according to a difference in oxygen concentration between the exhaust gas and the atmospheric gas, and estimate oxygen concentration based on the generated electromotive force.

Since the technology for sensing the concentration of oxygen contained in the exhaust gas through the oxygen sensor 100 is publicly known, the detailed descriptions thereof are omitted herein.

The voltage divider 200 may be positioned between the oxygen sensor 100 and the controller 300, and supply a voltage to the oxygen sensor 100 through voltage division.

The apparatus in accordance with the present embodiment may diagnose disconnection of the oxygen sensor 100 through a pulse signal based on control of the controller 300. At this time, the apparatus may diagnose disconnection of the oxygen sensor 100 by measuring the voltage supplied to the oxygen sensor 100 through the voltage divider 200 when a high or low-state pulse signal is applied to the oxygen sensor 100.

Specifically, the voltage divider 200 may be implemented with a circuit illustrated in FIG. 2. Thus, the apparatus in accordance with the embodiment may measure the voltage supplied to the oxygen sensor 100 through the voltage divider 200 when the pulse signal is off.

That is, based on the voltage divider 200 illustrated in FIG. 2, the voltage which is supplied to the oxygen sensor 100 when the pulse signal is off may be determined according to a resistance ratio R1 and R2 of the voltage divider 200. Therefore, when the oxygen sensor 100 is not disconnected, the voltage supplied to the resistor R2 and the voltage supplied to the oxygen sensor need to have the same value.

However, since the voltage divider 200 is not limited to the configuration illustrated in FIG. 2, the voltage divider 200 may include various circuits capable of supplying a voltage to the oxygen sensor 100 through voltage division for a specific voltage.

The controller 300 may diagnose disconnection of the oxygen sensor 100 through a pulse signal. As described above, the controller 300 may measure the voltage supplied to the oxygen sensor 100 through the voltage divider 200 when the pulse signal is off, and sense the voltage of the reference cell 120 of the oxygen sensor 100, thereby determining whether a ground wire of the oxygen sensor 100 is disconnected.

Specifically, when the voltage supplied to the oxygen sensor 100 and the voltage of the reference cell 120 deviate from preset reference values, respectively, the controller 300 may determine that the ground wire of the oxygen sensor 100 is disconnected.

That is, when the ground wire of the oxygen sensor 100 is normally connected, the voltage supplied to the oxygen sensor 100 needs to be equal to the voltage supplied to the resistor R2 of the voltage divider 200 based on Vcc of 5V. Thus, the controller 300 may determine whether the voltage supplied to the oxygen sensor 100 falls within a reference range from a first reference value.

At this time, the first reference value may indicate a voltage which is supplied to the resistor R2 according to the ratio of the resistors R1 and R2 based on Vcc, and the reference range may be set to a range including an error.

As described above, the voltage of the reference cell 120 needs to be constantly retained due to a pump current supplied from the pump cell 140. However, when the ground wire of the oxygen sensor 100 is disconnected, the pump current of the pump cell 140 cannot be normally supplied to the reference cell 120. Thus, the controller 300 may determine whether the voltage of the reference cell 120 falls within the reference range from a second reference value which is a target voltage based on the pump current.

At this time, the second reference value may indicate a voltage required for a normal operation of the reference cell 120 (typically 450 mV), and the reference range may be set to a range including an error.

In the above example, it has been described that the reference ranges for the first and second reference values are equal to each other. However, the present embodiment is not limited thereto, but the reference ranges may be set to different reference ranges.

The controller 300 may determine whether the ground wire of the oxygen sensor 100 was disconnected, based on the voltage supplied to the oxygen sensor 100 through the voltage divider 200 and the voltage of the reference cell 120 of the oxygen sensor 100.

In particular, when the oxygen sensor 100 is activated and an engine is normally driven, the controller 300 may measure the above-described voltages to determine whether the oxygen sensor 100 was disconnected.

That is, when the oxygen sensor 100 is not activated or the engine is not normally driven, the controller 300 may determine that the voltages deviate from the reference range, even though the oxygen sensor 100 was not disconnected.

Therefore, only when the oxygen sensor 100 is activated and the engine is normally driven, the controller 300 may determine whether the oxygen sensor 100 is disconnected. Specifically, when the temperature of the oxygen sensor 100 is equal to or more than a first reference temperature and the temperature of an exhaust pipe is equal to more than a second reference temperature, the controller 300 may determine that the oxygen sensor 100 is activated.

That is, a material stored in the oxygen sensor 100, such as titania, needs to be sufficiently heated in order to generate a sensitive electrical signal according to oxygen concentration. Thus, the controller 300 may determine whether the oxygen sensor 100 is heated over the first reference temperature at which the oxygen sensor 100 can normally sense oxygen concentration.

Since a lambda value (λ) of the oxygen sensor 100 can be constantly retained only when the exhaust pipe is sufficiently heated, the controller 300 may determine whether the temperature of the exhaust pipe is equal to or more than the second reference temperature at which the lambda value can be constantly retained.

Furthermore, when a battery voltage is equal to or more than a preset reference voltage, an engine RPM is equal to or more than a preset reference speed, and fuel injection of an injector is normally performed, the controller 300 may determine that the engine is normally driven.

That is, when a normal battery voltage is not supplied, the engine was not normally started, or fuel injection of the injector is not normally performed, the oxygen sensor 100 may output an unreliable sensing value because the engine is not normally driven.

Therefore, the controller 300 may determine whether the engine is normally operated through the above-described condition.

In the present embodiment, only under the condition that it can be determined that the oxygen sensor 100 is normally operated, the controller 300 may measure the voltage supplied to the oxygen sensor 100 and the voltage of the reference cell 120, thereby more precisely determining whether the oxygen sensor 100 is disconnected.

Therefore, the apparatus in accordance with the present embodiment may further include an input unit 400 configured to receive various signals for determining whether the oxygen sensor 100 is activated and the engine is normally driven.

Specifically, the input unit 400 may include a temperature measurement unit, a voltage measurement unit, an encoder, and a state sensor, which are not illustrated. The temperature measurement unit may measure the temperatures of the oxygen sensor 100 and the exhaust pipe, the voltage measurement unit may measure a battery voltage, the encoder may sense an engine RPM, and the state sensor may sense a fuel injection state of the injector.

Furthermore, in the present embodiment, the controller 300 may diagnose disconnection of the oxygen sensor 100 based on the voltage supplied to the oxygen sensor 100 and the voltage of the reference cell 120, and additionally diagnose disconnection of the oxygen sensor 100 based on the change in internal resistance of the oxygen sensor 100.

Specifically, the controller 300 may compare the internal resistances of the oxygen sensor 100 before and after the pumping current supplied to the reference cell 120 through the pump cell 140 of the oxygen sensor 100 is blocked, thereby determining whether the oxygen sensor 100 is disconnected.

That is, the controller 300 may measure the internal resistance of the oxygen sensor 100 before the pumping current is blocked, measure the internal resistance of the oxygen sensor 100 after the pumping current is blocked, and compare the measured internal resistances of the oxygen sensor 100.

In particular, before comparing the internal resistances of the oxygen sensor 100 before and after the pumping current is blocked, the controller 300 may preferentially fix a heating duty of the oxygen sensor 100, and measure the internal resistances.

That is, when the heating duty of the oxygen sensor 100 is changed, the sensitivity of the internal resistance which reacts to the oxygen concentration may differ. Then, the oxygen sensor 100 may generate different outputs even though the same inputs are supplied. Thus, in the present embodiment, the controller 300 may measure and compare the internal resistances in a state where the heating duty is retained at the same value.

Since the heating duty is retained at the same value, the internal resistance of the oxygen sensor 100 needs to be constantly retained, regardless of whether the pumping current is supplied. However, when the ground wire of the oxygen sensor 100 is disconnected, the internal resistance of the oxygen sensor 100 may be measured at a different value.

Therefore, in the present embodiment, the controller 300 may fix the heating duty of the oxygen sensor 100, and then compare the internal resistances of the oxygen sensor 100 before and after the pumping current supplied to the reference cell 120 is blocked. Thus, the controller 300 may additionally verify whether the oxygen sensor 100 is disconnected.

That is, the controller 300 may primarily diagnose disconnection of the oxygen sensor 100, based on the voltage supplied to the oxygen sensor 100 and the voltage of the reference cell 120, and secondarily diagnose disconnection of the oxygen sensor 100 by comparing the internal resistances of the oxygen sensor 100.

FIG. 3 is a flowchart for describing a method for diagnosing disconnection of an oxygen sensor in accordance with an embodiment of the present invention.

Referring to FIG. 3, the method for diagnosing disconnection of an oxygen sensor in accordance with the embodiment of the present invention will be described. First, the controller 300 may determine whether a monitoring condition for diagnosing disconnection of the oxygen sensor 100 is satisfied, at step S10.

Specifically, when the oxygen sensor 100 is activated and the engine is normally driven, the controller 300 may determine that the monitoring condition for diagnosing disconnection is satisfied.

That is, when the oxygen sensor 100 is not activated or the engine is not normally driven, the controller 300 may determine that the oxygen sensor 100 is disconnected, even though the oxygen sensor 100 is not disconnected.

Therefore, only when the oxygen sensor 100 is activated and the engine is normally driven, the controller 300 may determine whether the oxygen sensor 100 is disconnected. Specifically, when the temperature of the oxygen sensor 100 is equal to or more than the first reference temperature and the temperature of the exhaust pipe is equal to more than the second reference temperature, the controller 300 may determine that the oxygen sensor 100 is activated.

That is, a material stored in the oxygen sensor 100, such as titania, needs to be sufficiently heated in order to generate a sensitive electrical signal according to oxygen concentration. Thus, the controller 300 may determine whether the oxygen sensor 100 is heated over the first reference temperature at which the oxygen sensor 100 can normally sense oxygen concentration.

Since a lambda value (λ) of the oxygen sensor 100 can be constantly retained only when the exhaust pipe is sufficiently heated, the controller 300 may determine whether the temperature of the exhaust pipe is equal to or more than the second reference temperature at which the lambda value can be constantly retained.

Furthermore, when a battery voltage is equal to or more than the preset reference voltage, an engine RPM is equal to or more than the preset reference speed, and fuel injection of the injector is normally performed, the controller 300 may determine that the engine is normally driven.

That is, when a normal battery voltage is not supplied, the engine was not normally started, or the fuel injection of the injector is not normally performed, the oxygen sensor 100 may be unstably operated, and output an unreliable sensing value.

Then, the controller 300 may measure the voltage supplied to the oxygen sensor 100 through the voltage divider 200 at step S20, and measure the voltage of the reference cell 120 of the oxygen sensor 100 at step S30.

The controller 300 may determine whether the voltages measured at the above-described steps S20 and S30 fall within the reference range from the respective reference values, at step S40.

That is, when the ground wire of the oxygen sensor 100 is normally connected, the voltage supplied to the oxygen sensor 100 needs to be equal to the voltage supplied to the resistor R2 of the voltage divider 200. Thus, the controller 300 may determine whether the voltage supplied to the oxygen sensor 100 falls within the reference range from the first reference value which is supplied to the resistor R2 according to the ratio of the resistors R1 and R2.

Furthermore, the voltage of the reference cell 120 needs to be constantly retained due to a pump current supplied from the pump cell 140. However, when the ground wire of the oxygen sensor 100 is disconnected, the pump current of the pump cell 140 cannot be normally supplied to the reference cell 120. Thus, the controller 300 may determine whether the voltage of the reference cell 120 falls within the reference range from the second reference value corresponding to a target voltage of the reference cell 120, at which the pump current is intended to be retained.

When it is determined at step S40 that any one of the voltage supplied to the oxygen sensor 100 and the voltage of the reference cell 120 deviates from the reference range from each of the reference values, the controller 300 may determine that the ground wire of the oxygen sensor 100 is disconnected.

Furthermore, in the present embodiment, the controller 300 may compare the internal resistances of the oxygen sensor 100 before and after the pumping current supplied to the reference cell 120 through the pump cell 140 is blocked, thereby improving the precision of the operation for diagnosing disconnection of the oxygen sensor 100.

Specifically, the controller 300 may fix the heating duty of the oxygen sensor 100 at step S50, measure the internal resistance of the oxygen sensor 100 at step S60, block the pumping current of the oxygen sensor 100 at step S70, and measure the internal reference of the oxygen sensor 100 again at step S80.

That is, when the heating duty of the oxygen sensor 100 is changed, the sensitivity of the internal resistance which reacts to the oxygen concentration may differ. In this case, the oxygen sensor 100 may generate difference outputs even though the same inputs are supplied. Thus, in the present embodiment, the controller 300 may measure and compare the internal resistances in a state where the heating duty is retained at the same value.

Since the heating duty is retained at the same value, the internal resistances of the oxygen sensor 100 need to be constantly retained, regardless of whether the pumping current is supplied. However, when the ground wire of the oxygen sensor 100 is disconnected, the internal resistances of the oxygen sensor 100 may be measured at different values.

Therefore, the controller 300 may determine whether a difference between the internal resistances of the oxygen sensor 100, measured at step S60 and 80, falls within the error range at step S90. When the difference deviates from the error range, the controller 300 may diagnose that the ground wire of the oxygen sensor 100 is disconnected, at step S100.

In accordance with the present embodiment, the controller can accurately diagnose disconnection of the ground wire of the oxygen sensor through various measured values, and maintain the oxygen sensor in an optimal state.

Furthermore, since the controller diagnoses disconnection of the oxygen sensor after the oxygen sensor is normally activated, the controller can minimize a diagnosis error which may occur when diagnosing disconnection of the oxygen sensor.

Although preferred embodiments of the invention have been disclosed for illustrative purposes, those skilled in the art will appreciate that various modifications, additions and substitutions are possible, without departing from the scope and spirit of the invention as defined in the accompanying claims.

What is claimed is:

1. A method for diagnosing disconnection of an oxygen sensor, comprising:
   measuring, by a controller, a voltage supplied to an oxygen sensor through a voltage divider;
   measuring, by the controller, a voltage of a reference cell of the oxygen sensor;
   determining, by the controller, whether the voltage supplied to the oxygen sensor and the voltage of the reference cell fall within reference ranges from preset reference values, respectively; and determining, by the controller, that a ground wire of the oxygen sensor is disconnected, when the voltage supplied to the oxygen sensor or the voltage of the reference cell deviates from its reference range.

2. The method of claim 1, further comprising, by the controller, determining whether the oxygen sensor is activated and an engine is normally driven, before measuring the voltage supplied to the oxygen sensor, wherein when the oxygen sensor is activated and the engine is normally driven, the controller measures the voltage supplied to the oxygen sensor.

3. The method of claim 2, wherein in the determining of whether the oxygen sensor is activated and the engine is normally driven, the controller determines that the oxygen sensor is activated when the temperature of the oxygen sensor is equal to or more than a first reference temperature and the temperature of an exhaust pipe is equal to or more than a second reference temperature, and determines that the engine is normally driven when a battery voltage is equal to or more than a preset reference voltage, an engine RPM is equal to or more than a preset reference speed, and fuel injection of an injector is normally performed.

4. The method of claim 1, further comprising, by the controller, comparing internal resistances of the oxygen sensor before and after a pumping current supplied to the reference cell through a pump cell of the oxygen sensor is blocked, before determining that the ground wire of the oxygen sensor is disconnected, wherein when a difference between the internal resistances before and after the pumping current is blocked deviates from a preset error range, the controller determines that the ground wire of the oxygen sensor is disconnected.

5. The method of claim 4, wherein the comparing of the internal resistances of the oxygen sensor before and after the pumping current is blocked comprises:

fixing, by the controller, a heating duty of the oxygen sensor;

measuring the internal resistance of the oxygen sensor before the pumping current is blocked;

measuring the internal resistance of the oxygen sensor after the pumping current is blocked; and comparing the measured internal resistances of the oxygen sensor.

6. An apparatus for diagnosing disconnection of an oxygen sensor, comprising:

an oxygen sensor comprising a reference cell, a pump cell, and a measurement cell;

a voltage divider configured to supply a voltage to the oxygen sensor through voltage division; and a controller configured to diagnose disconnection of the oxygen sensor, wherein the controller measures the voltage supplied to the oxygen sensor through the voltage divider, senses a voltage of the reference cell of the oxygen sensor, and determines that a ground wire of the oxygen sensor is disconnected when the voltage supplied to the oxygen sensor and the voltage of the reference cell deviate from reference ranges from preset reference values, respectively.

7. The apparatus of claim 6, wherein the controller measures the voltage supplied to the oxygen sensor when the oxygen sensor is activated and an engine is normally driven, and the apparatus further comprises an input unit configured to receive various signals for determining whether the oxygen sensor is activated and the engine is normally driven.

8. The apparatus of claim 7, wherein the controller determines that the oxygen sensor is activated when the temperature of the oxygen sensor is equal to or more than a first reference temperature and the temperature of an exhaust pipe is equal to or more than a second reference temperature, and determines that the engine is normally driven when a battery voltage is equal to or more than a preset reference voltage, an engine RPM is equal to or more than a preset reference speed, and fuel injection of an injector is normally performed.

9. The apparatus of claim 6, wherein the controller compares internal resistances of the oxygen sensor before and after a pumping current supplied to the reference cell through the pump cell of the oxygen sensor is blocked, and determines that the ground wire of the oxygen sensor is disconnected when a difference between the internal resistances before and after the pumping current is blocked deviates from a preset error range.

10. The apparatus of claim 9, wherein the controller fixes a heating duty of the oxygen sensor, and measures the internal resistance of the oxygen sensor before the pumping current is blocked.

* * * * *